(12) United States Patent
Jia et al.

(10) Patent No.: US 7,906,564 B2
(45) Date of Patent: Mar. 15, 2011

(54) SELF ETCH ALL PURPOSE DENTAL CEMENT COMPOSITION, METHOD OF MANUFACTURE, AND METHOD OF USE THEREOF

(75) Inventors: Weitao Jia, Wallingford, CT (US); Shuhua Jin, Wallingford, CT (US)

(73) Assignee: Pentron Clinical Technologies, LLC, Wallingford, CT (US)

( * ) Notice: Subject to any disclaimer, the term of this patent is extended or adjusted under 35 U.S.C. 154(b) by 595 days.

(21) Appl. No.: 11/360,314

(22) Filed: Feb. 23, 2006

(65) Prior Publication Data

US 2007/0197682 A1  Aug. 23, 2007

(51) Int. Cl.
  *A61K 6/083* (2006.01)
  *A61C 5/00* (2006.01)
(52) U.S. Cl. ........................ 523/116; 523/118; 433/228.1
(58) Field of Classification Search .................. 523/116, 523/118; 433/228.1
  See application file for complete search history.

(56) References Cited

U.S. PATENT DOCUMENTS

| | | |
|---|---|---|
| 4,148,988 A | 4/1979 | Masuhara et al. |
| 4,306,913 A | 12/1981 | Mabie et al. |
| 4,503,169 A | 3/1985 | Randklev |
| 4,544,359 A | 10/1985 | Waknine |
| 4,547,531 A | 10/1985 | Waknine |
| 4,593,054 A | 6/1986 | Asmussen et al. |
| 4,659,751 A | 4/1987 | Bowen |
| 4,691,045 A | 9/1987 | Fukuchi et al. |
| 4,719,149 A | 1/1988 | Aasen et al. |
| 4,802,950 A | 2/1989 | Croll |
| 4,880,660 A | 11/1989 | Aasen et al. |
| 5,061,183 A | 10/1991 | Nicholson |
| 5,171,763 A | 12/1992 | Ohno et al. |
| 5,256,065 A | 10/1993 | Nicholson |
| 5,260,476 A | 11/1993 | Ohno et al. |
| 5,264,513 A | 11/1993 | Ikemura et al. |
| 5,276,068 A | 1/1994 | Waknine |
| 5,348,988 A | 9/1994 | Suh et al. |
| 5,444,104 A | 8/1995 | Waknine |
| 5,525,648 A | 6/1996 | Aasen et al. |
| 5,756,560 A | 5/1998 | Antonucci et al. |
| 5,865,623 A | 2/1999 | Suh |
| 5,925,690 A | 7/1999 | Fuchigami et al. |
| 5,954,996 A | 9/1999 | Discko, Jr. |
| 5,969,000 A | 10/1999 | Yang et al. |
| 6,004,390 A | 12/1999 | Pflug et al. |
| 6,013,694 A | 1/2000 | Jia et al. |
| 6,071,983 A | 6/2000 | Yamamoto et al. |
| 6,147,137 A | 11/2000 | Jia |
| 6,217,644 B1 | 4/2001 | Matsunae et al. |
| 6,270,562 B1 | 8/2001 | Jia |
| 6,291,548 B1 | 9/2001 | Akahane et al. |
| 6,312,667 B1 | 11/2001 | Trom et al. |
| 6,355,704 B1 | 3/2002 | Nakatsuka et al. |
| 6,403,676 B1 | 6/2002 | Jia et al. |
| 6,417,246 B1 | 7/2002 | Jia et al. |
| 6,572,693 B1 | 6/2003 | Wu et al. |
| 6,653,365 B2 | 11/2003 | Jia |
| 6,673,958 B2 | 1/2004 | Tiba et al. |
| 6,730,715 B2 | 5/2004 | Jia |
| 6,759,449 B2 | 7/2004 | Kimura et al. |
| 6,815,470 B2 | 11/2004 | Ibaragi et al. |
| 6,939,900 B2 | 9/2005 | Ario et al. |
| 7,166,651 B2 * | 1/2007 | Qian .............................. 523/115 |
| 7,214,726 B2 * | 5/2007 | Qian .............................. 523/116 |
| 7,304,096 B2 * | 12/2007 | Han et al. ....................... 522/100 |
| 2002/0082317 A1 | 6/2002 | Lyons et al. |
| 2003/0055124 A1 | 3/2003 | Klee et al. |
| 2003/0207960 A1 | 11/2003 | Jia |
| 2004/0054027 A1 | 3/2004 | Lyons et al. |
| 2004/0156795 A1 | 8/2004 | Nemoto et al. |
| 2004/0229973 A1 | 11/2004 | Sang et al. |
| 2004/0235981 A1 | 11/2004 | Qian |
| 2005/0014861 A1 | 1/2005 | Qian |
| 2005/0020720 A1 | 1/2005 | Dickens et al. |
| 2005/0049326 A1 | 3/2005 | Park et al. |
| 2005/0192374 A1 | 9/2005 | Jia et al. |
| 2005/0277706 A1 | 12/2005 | Han et al. |
| 2007/0197683 A1 | 8/2007 | Jia et al. |
| 2007/0299157 A1 | 12/2007 | Sang et al. |
| 2008/0242761 A1 | 10/2008 | Jia et al. |

OTHER PUBLICATIONS

The International Searching Authority, International Search Report, PCT/US2007/004458, Mailing Date: Mar. 27, 2008, 7 pages.
The International Searching Authority, Written Opinion of the International Searching Authority, PCT/US2007/004458, Mailing Date: Mar. 27, 2008, 7 pages.
S. Venz and B. Dickens: Modified Surface-Active Monomers for Adhesive bonding to Dentin; J Dent Res 72 (3):582-586, Mar. 1993: PMGDM resin.

* cited by examiner

*Primary Examiner* — Tae H Yoon
(74) *Attorney, Agent, or Firm* — Wood, Herron & Evans, LLP

(57) ABSTRACT

A self-etching, dental cement composition is provided having the advantage of not requiring a separate etching and bonding step.

19 Claims, No Drawings

SELF ETCH ALL PURPOSE DENTAL CEMENT COMPOSITION, METHOD OF MANUFACTURE, AND METHOD OF USE THEREOF

TECHNICAL FIELD

This invention relates to dental resin cement compositions comprising polymerizable (meth)acrylate resins, their method of manufacture, and the use of such resins for restorative dentistry without the need for a separate etching/bonding step.

BRIEF DESCRIPTION OF THE RELATED ART

Methods and compositions for improving the adhesion of resins to hard tissue, i.e., dentin or enamel, is an ongoing goal in the dental arts. Improved adhesion leads to longer lasting restorations and reduced tooth sensitivity. Numerous methods for preparing teeth for the application of a dental restorative material (such as a sealant, filling material, cementation of indirect dental restorations or the like) have accordingly been developed, including acid etch and priming steps.

Acid etchants are commonly used to remove a smear layer and demineralize the tooth surfaces so as to promote effective mechanical bonding of the restorative material. However, the use of an etchant has a disadvantage in that it must be washed off after application, requiring the time-consuming procedure of application, washing, and drying. A further disadvantage of etchants is the perception that use of strong etchants can increase dental sensitivity in some patients.

In addition to acid etch procedures, adhesive strength is also improved by use of a primer. Primers are generally surface-active compounds that exhibit both an affinity for dentin and adhesive resin systems and participate in the polymerization process, thereby promoting adhesion between the primarily hydrophilic dentin and the predominantly hydrophobic polymeric adhesives or monomers from which they are formed. Primers are applied to dentin in solution form, commonly used solvents including acetone, ethanol, water, and various mixed solvent systems. While effective for promoting bonding, primers however are often applied using an additional step.

Current resin cement materials used for the cementation of dental restorations made from metal alloy, ceramic/porcelain, or composite material require a separate bonding procedure to ensure sufficient and effective bonding of the dental restoration to the tooth. Often a separate procedure including etching and applying a bonding adhesive to the tooth or restoration is required, rendering the cementation procedure time consuming and more complex.

Conventional luting cements such as glass ionomer cement, zinc phosphate cement, and polycarboxylate cement are typically used for cementing metal restorations without a separate bonding step. However, the luting cements are not suitable for cementing composite or ceramic restorations. Additionally, the bonding ability of the luting cements to tooth structure is poor.

There accordingly remains a need in the art for improved dental cement materials providing improved adhesion to a tooth surface and a dental substrate, and yet which can be applied in a fewer number of steps.

SUMMARY OF THE INVENTION

The above-described drawbacks and disadvantages are alleviated by a self-etching and bonding dental resin cement composition comprising a polymerizable (meth)acrylate carboxylic acid/anhydride; a copolymerizable multi-functional (meth)acrylate; a diluent; a filler; and a curing system. These cement compositions can be prepared as a two-paste system that is combined prior to use.

Specifically, a self-etching and bonding dental resin cement composition comprises a two paste system that is combined prior to use, wherein a first paste comprises about 40 to about 80 weight percent of a polymerizable (meth)acrylate carboxylic acid/anhydride based on the total weight of the first paste polymerizable material; a first copolymerizable multi-functional (meth)acrylate; a first diluent; a first filler; and a peroxide curing system; wherein a second paste comprises a second copolymerizable multi-functional (meth)acrylate; a second diluent; a second filler; optionally a second polymerizable (meth)acrylate carboxylic acid/anhydride; and optionally a photoinitiator.

The self-etching and bonding dental resin cement composition provides even further advantages over the art, as all etching and bonding can be performed in one step without the need for the use of an etchant or a separate bonding adhesive. Furthermore, the self-etching and bonding dental resin cement composition can be both self-curable and light curable.

In accordance with the method of use, the self-etching and bonding dental resin cement composition is physically contacted with the tooth structure or a tooth restoration, the tooth restoration is then adhered to the tooth surface, and the cement composition is allowed to cure.

DETAILED DESCRIPTION OF THE PREFERRED EMBODIMENTS

Described herein are self-etching and bonding dental resin cement compositions that will, in one operation, etch the tooth surface, i.e. remove dentin smear and etch/dissolve calcium minerals from the surface of the tooth structure, and bond a tooth restoration to the tooth. As the cement composition is self-etching and bonding, the resin cement coating forms a reliable bond with the tooth structure and a tooth restoration. The composition can accordingly be used without intermediate adhesion steps.

Specifically, a self-etching and bonding dental resin cement composition comprises a two paste system that is combined prior to use, wherein a first paste comprises about 40 to about 80 weight percent of a polymerizable (meth)acrylate carboxylic acid/anhydride based on the total weight of the first paste polymerizable material; a first copolymerizable multi-functional (meth)acrylate; a first diluent; a first filler; and a peroxide curing system; wherein a second paste comprises a second copolymerizable multi-functional (meth)acrylate; a second diluent; a second filler; optionally a photoinitiator; and optionally a second polymerizable (meth)acrylate carboxylic acid/anhydride.

The polymerizable (meth)acrylate carboxylic acid/anhydride can have the general structure according to structure (I):

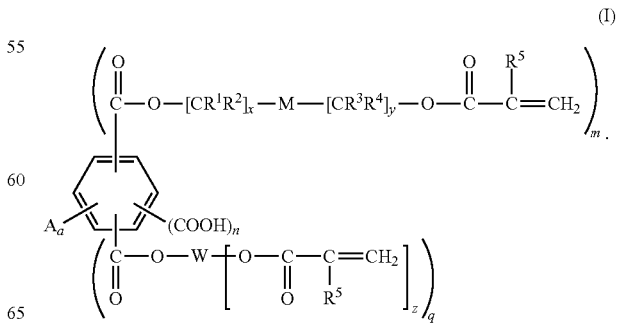

In structure (I), n is 0, 1, 2, 3, or 4; q is 1, 2, 3, or 4; A is an anhydride group; and a is 0 or 1, with the proviso that a and n are not both 0 at the same time. As is known, the anhydride group (—C(O)—O—C(O)—) is linked via its two carbon atoms to two ortho carbons of the phenyl ring.

Further in structure (I), $R^1$, $R^2$, $R^3$, and $R^4$ are each independently hydrogen, hydroxy, $C_1$-$C_{12}$ alkyl, $C_1$-$C_{12}$ perhaloalkyl, $C_1$-$C_{12}$ alkoxy, $C_1$-$C_{12}$ perhaloalkoxy, $C_2$-$C_{12}$ alkenyl, $C_2$-$C_{12}$ alkynyl, ($C_1$-$C_6$ alkyl)-O—($C_1$-$C_6$ alkylene), or hydroxy($C_1$-$C_6$ alkylene), wherein x and y are each independently an integer from 1 to 10. In one embodiment, $R^1$, $R^2$, $R^3$, and $R^4$ are each independently hydrogen, hydroxy, or $C_1$-$C_{12}$ alkyl, and x and y is each independently an integer from 1 to 6. More specifically, $R^1$, $R^2$, $R^3$, and $R^4$ is each independently hydrogen or $C_1$-$C_6$ alkyl.

$R^5$ in structure (I) is a hydrogen or methyl group, and specifically methyl group.

M in structure (I) is a carbonyl-containing group, in particular

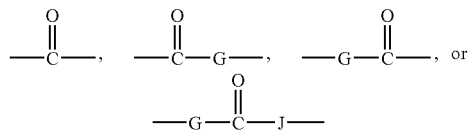

wherein G and J are each independently oxygen or $NR^6$, wherein R is hydrogen or $C_1$-$C_6$ alkyl; and m is 0, 1, or 2. Specifically, M is

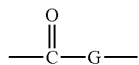

wherein G is oxygen. m is 0 or 1.

W in structure (I) is a hydrocarbyl linking group having a valency corresponding to z, the number of (meth)acrylate groups, plus one; specifically z is 1, 2, 3, 4, or 5. W may be aromatic or aliphatic, specifically aliphatic. Suitable aromatic groups are phenyl and napthyl, and suitable aliphatic groups are $C_1$-$C_{12}$ alkyl, cycloalkyl, alkenyl, or alkynyl groups.

In structure (I), when a is 0, n is 1, 2, 3, or 4 and n+m+q is 2, 3, 4, 5, or 6. When a is 1, n is 0, 1, 2, or 3, and n+m+q is 1, 2, 3, or 4. When n is 0, a is 1, and m+q is 1, 2, 3, or 4.

In one embodiment, polymerizable (meth)acrylate carboxylic acid/anhydride has the general structure according to structure (I), wherein a is 0 or 1; n is 0, 1, or 2; m is 0 or 1; q is 1 or 2; A is an anhydride group; $R^1$, $R^2$, $R^3$, and $R^4$ are each independently hydrogen, hydroxy, or $C_1$-$C_{12}$ alkyl; x and y is each independently an integer 1, 2; or 3; $R^5$ is a hydrogen or methyl group; M is a carbonyl-containing group, in particular

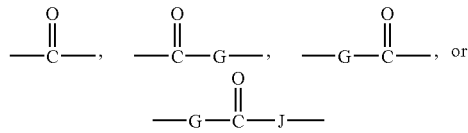

wherein G and J are each independently oxygen or $NR^6$, wherein $R^6$ is hydrogen or $C_1$-$C_6$ alkyl; W is an aliphatic hydrocarbyl linking group having a valency corresponding to z, the number of (meth)acrylate groups, plus one; specifically z is 1, 2, or 3; with the proviso that both a and n are not both 0.

In another embodiment, the polymerizable (meth)acrylate carboxylic acid/anhydride has the general structure according to structure (II):

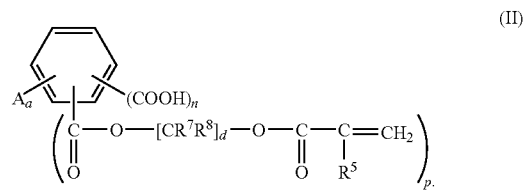

In structure (II), n is 0, 1, 2, 3, or 4; A is an anhydride group; a is 0 or 1; and $R^5$ is hydrogen or methyl, with the proviso that a and n are not both 0 at the same time. p is 1, 2, 3, or 4, specifically 1, 2, or 3, and more specifically 1 or 2. $R^7$ and $R^8$ are each independently hydrogen, hydroxy, $C_1$-$C_{12}$ alkyl, $C_1$-$C_{12}$ perhaloalkyl, $C_1$-$C_{12}$ alkoxy, $C_1$-$C_{12}$ perhaloalkoxy, $C_2$-$C_{12}$ alkenyl, $C_2$-$C_{12}$ alkynyl, ($C_1$-$C_6$ alkyl)-O—($C_1$-$C_6$ alkylene), or hydroxy($C_1$-$C_6$ alkylene), specifically $R^7$ and R8 are each independently hydrogen, hydroxy, or $C_1$-$C_{12}$ alkyl, more specifically $R^7$ and $R^8$ are each independently hydrogen, hydroxy, $C_1$-$C_6$ alkyl. d is an integer of 1 to 10, specifically 1, 2, 3, 4, or 5, and more specifically 1, 2, or 3.

In structure (II), when a is 0, n is 1, 2, 3, or 4. When a is 1, n is 0, 1, 2, or 3. When n is 0, a is 1.

In one embodiment, for structure (II) n is 0, 1, 2, or 3; A is an anhydride group; a is 0 or 1; $R^5$ is hydrogen or methyl; p is 1, 2, or 3; $R^7$ and $R^8$ are each independently hydrogen, hydroxy, or $C_1$-$C_{12}$ alkyl; d is 1, 2, 3, 4, or 5; and with the proviso that a and n are not both 0.

Exemplary polymerizable (meth)acrylate carboxylic acid/anhydrides encompassed by the structure (I) include 1,4-di(meth)acryloyloxyethylpyromellitic acid; 4-(meth)acryloyloxymethyltrimellitic acid and the anhydride thereof; 4-methacryloyloxyethyltrimellitic acid (4-MET) and an anhydride thereof (4-META); 4-acryloyloxyethyltrimellitic acid and an anhydride thereof, 4-(2-hydroxy-3-(meth)acryloyloxy)butyltrimellitic acid and an anhydride thereof; an adduct of 2-hydroxyethyl methacrylate (HEMA) with pyromellitic dianhydride (PMDM); an adduct of 2-hydroxyethyl acrylate with pyromellitic dianhydride; the reaction product of HEMA with ethylene glycol bistrimellitate dianhydride (EDMT); the adduct of pyromellitic dianhydride with glycerol dimethacrylate (PMGDM); or a combination comprising at least one of the foregoing.

The polymerizable (meth)acrylate (I) may be synthesized, for example, from the reaction of a hydroxy-containing (meth)acrylate monomer and an aromatic compound comprising anhydride or carboxylic acid functionality or their synthetic equivalents (e.g., a carboxylic acid halide, for example chloride). Exemplary synthetic methods are described in U.S. Published Application, 2005/0192374A1 incorporated herein by reference in its entirety.

The polymerizable (meth)acrylate carboxylic acid/anhydride is present in the first paste at about 40 to about 80 weight percent, specifically about 45 to about 70 weight percent, more specifically about 50 to about 65 weight percent, and still yet more specifically about 55 to about 60 weight percent based on the total weight of the first paste polymerizable material. As used herein, "polymerizable material" includes any compound that can copolymerize with the (meth)acrylate functionality of the polymerizable (meth)acrylate carboxylic acid/anhydride, such as compounds comprising ethylenically unsaturated groups, for example, the copolymerizable multi-functional (meth)acrylates, the diluents, co-polymerizable adhesion promoter, and the like.

As used herein, the term "(meth)acrylate" is intended to encompass both acrylate and methacrylate groups.

Optionally, the polymerizable (meth)acrylate carboxylic acid/anhydride may also be present in the second paste in an amount of about 1 to about 40 weight percent, specifically about 2 to about 30 weight percent, more specifically about 3 to about 20 weight percent, and still yet more specifically about 4 to about 10 weight percent based on the total weight of the second paste polymerizable material.

The self-etching and bonding dental resin cement composition further comprises a copolymerizable multi-functional (meth)acrylate present in the first and second paste systems. The copolymerizable multi-functional (meth)acrylate may be monomeric, oligomeric, or polymeric, and has a (meth)acrylate functionality that is copolymerizable with the polymerizable (meth)acrylate carboxylic acid/anhydride, specifically two or more (meth)acrylate functionalities. The copolymerizable multi-functional (meth)acrylates differ from the diluent monomers as they are viscous resins, and include, for example, urethane(meth)acrylates, including urethane dimethacrylate (UDMA); polyurethane(meth)acrylates, including polyurethane dimethacrylate (PUDMA); diurethane dimethacrylates, including diurethane di(meth)acrylate (DUDMA); polycarbonate di(meth)acrylates, including the polycarbonate dimethacrylate (PCDMA) disclosed in U.S. Pat. No. 5,276,068 and 5,444,104 to Waknine, which is the condensation product of two parts of a hydroxyalkylmethacrylate and 1 part of a bis(chloroformate); ethoxylated bisphenol A di(meth)acrylates including ethoxylated bisphenol A dimethacrylate (EBPDMA) as disclosed in U.S. Pat. No. 6,013,694 to Jia, et al.; ethoxylated trimethylolpropane tri(meth)acrylates, specifically having about 10 to about 30 ethoxy groups; the diglycidyl(meth)acrylate adducts of Bisphenol A, including 2,2'-bis [4-(3-methacryloxy-2-hydroxy propoxy)-phenyl]-propane (BisGMA); or a combination comprising at least one of the foregoing. Either or both of the pastes can contain more than one type of multi-functional (meth)acrylate.

The total amount of first copolymerizable multi-functional (meth)acrylate present in the first paste can be about 0.01 to about 30 weight percent, specifically about 1 to about 25 weight percent, and more specifically about 5 to about 20 weight percent based on the total weight of the first paste polymerizable material.

The total amount of second copolymerizable multi-functional (meth)acrylate present in the second paste can be about 20 to about 95 weight percent, specifically about 50 to about 90 weight percent, and more specifically about 65 to about 80 weight percent based on the total weight of the second paste polymerizable material.

The self-etching and bonding dental resin cement composition further comprises a diluent monomer in the first and second paste. Diluent monomers may be used to increase the surface wettability of the composition and/or to decrease the viscosity of the polymerization medium. Suitable diluent monomers include, for example: hydroxyalkyl(meth)acrylates, for example 2-hydroxyethyl(meth)acrylate, 2-hydroxypropyl(meth)acrylate, and 4-hydroxybutyl(meth)acrylate, specifically HEMA; ethylene glycol mono- and di(meth)acrylates, including ethylene glycol(meth)acrylate, diethylene glycol(meth)acrylate, tri(ethylene glycol) di(meth)acrylate, specifically tri(ethylene glycol) dimethacrylate (TEGDMA), and tetra(ethylene glycol) di(meth)acrylate; propylene glycol mono- and di-(meth)acrylates, both 1,2- and 1,3-, including propylene glycol(meth)acrylate, dipropylene glycol(meth)acrylate, tri(propylene glycol) di(meth)acrylate, and tetra(propylene glycol) di(meth)acrylate; diol di(meth) acrylates such as 1,4-butanediol di(meth)acrylate, dodecane diol di(meth)acrylate, and 1,6-hexanediol di(meth)acrylate; glycerol mono- and di(meth)acrylates; trimethylolpropane mono-, di-, and tri-(meth)acrylates; pentaerythritol mono-, di-, and tri-(meth)acrylates; phenyl glycidyl ether(meth)acrylate; or a combination comprising at least one of the foregoing.

The total amount of first diluent in the first paste can be about 1 to about 60 weight percent, specifically about 5 to about 50 weight percent, and more specifically about 10 to about 40 weight percent based on the total weight of the first paste polymerizable material.

The total amount of second diluent in the second paste can be about 5 to about 50 weight percent, specifically about 10 to about 40 weight percent, and more specifically about 20 to about 30 weight percent based on the total weight of the second paste polymerizable material.

The self-etching and bonding dental resin cement composition may further optionally comprise a co-polymerizable adhesion promoter, for example an olefinically unsaturated monomer resin containing a phosphoryl group. Exemplary copolymerizable adhesion promoters include dipentaerythritol-pentaacrylate-phosphoric acid ester (PENTA); bis(2-ethylhexyl)hydrogen phosphate; 2-(methacryloyloxy)-ethyl phosphate; or a combination comprising at least one of the foregoing adhesion promoters.

The self-etching and bonding dental resin cement composition further contains a curing system, which generally can include polymerization initiators; polymerization accelerators; ultraviolet light absorbers; antioxidants; and/or other additives known in the art depending upon whether the cement composition is formulated for self-cure or dual-cure.

The self-cure composition can be cured without the use of radiation activation. Such curing systems typically include a free radical polymerization initiator such as, for example, a peroxide in an amount of about 0.1 to about 5.0 parts per hundred based on the total of the polymerizable materials of the first or second paste. Exemplary free radical polymerization initiators are lauryl peroxide, tributyl hydroperoxide, and benzoyl peroxide (BPO).

The dual-cure system is both self-cure and radiation cure, for example, the self-etching and bonding dental resin cement composition is actinic light curable, specifically ultraviolet (UV) or visible light. Suitable free radical polymerization initiators for visible light-curable compositions employ light-sensitive compounds, including for example, benzil, benzoin, benzoin methyl ether, DL-camphorquinone (CQ), and benzil diketones. Suitable commercially available phosphine oxide photoinitiators include, for example, the LUCIIN™ series from BASF Corp. such as LUCIRIN™ TPO (L-TPO) and LUCIRIN™ 8809. Other phosphine oxide photoinitiators may be selected from the DAROCUR™ or IRGACURE™ series from Ciba-Geigy Corp. Examples include DAROCUR™ TPO, DAROCUR™ 4265, IRGACURE™ 1800, and the like. Either UV-activated cure or visible light-activated cure (approximately 230 to 750 nanometer) is acceptable. The amount of photoinitiator is selected according to the curing rate desired. A minimal catalytically effective amount is generally about 0.01 weight percent of the total self-etching and bonding dental resin cement composition, and will lead to a slower cure. Faster rates of cure are achieved with amounts of catalyst in the range from greater than about 0.1 to about 5 parts per hundred based on the total of the polymerizable materials of the first or second paste.

Optionally, an ultraviolet absorber can be used in the curing system in an amount of about 0.05 to about 5.0 parts per hundred based on the total of the polymerizable materials of the first or second paste. Such UV absorbers are useful in the visible light-curable dental restorative materials in order to avoid discoloration of the resin from incident ultraviolet light. Suitable UV absorbers are the various benzophenones, particularly UV-5411 available from American Cyanamid Company.

Free radical-type polymerization accelerators suitable for use in the curing system include the various organic tertiary amines well known in the art. In visible light-curable compositions, the tertiary amines are generally (meth)acrylate derivatives such as dimethylaminoethyl methacrylate and, specifically, diethylaminoethyl methacrylate (DEAEMA) or tertiary aromatic amines such as ethyl 4-(dimethylamino) benzoate (EDMAB) in an amount of about 0.5 to about 5.0 parts per hundred based on the total of the polymerizable materials of the first or second paste. In the self-curing compositions, the tertiary amines are generally aromatic tertiary amines, specifically tertiary aromatic amines such as EDMAB, 2-[4-(dimethylamino)phenyl]ethanol, N,N-dimethyl-p-toluidine (DMPT), and bis(hydroxyethyl)-p-toluidine (DHEPT). Other exemplary accelerators include aromatic sulfinic acid salts, for example benzenesulfinic acid, sodium salt (BSA.Na). Such accelerators are generally present in an amount of about 0.5 to about 4.0 parts per hundred based on the total of the polymerizable materials of the first or second paste.

The self-etching and bonding dental resin cement composition further comprises a filler system comprising one or more of the inorganic fillers suitable for use in dental composite materials. Examples of suitable filling materials include but are not limited to, silica including fumed silica, quartz, strontium silicate, strontium borosilicate, lithium silicate, lithium alumina silicate, amorphous silica, ammoniated or deammoniated calcium phosphate, tricalcium phosphate, alumina, zirconia, tin oxide, titania, barium-boro-silicate glass filler, glass ionomer filler (e.g. Ca—Al—F—Ba-Silicate) and a combination comprising at least one of the foregoing fillers. Some of the aforementioned inorganic filling materials and methods of preparation thereof are known in the art, as disclosed in U.S. Pat. No. 4,544,359 and No. 4,547,531 to Waknine, pertinent portions of which are incorporated herein by reference. Organic-inorganic fillers of POSS™ (Hybrid Plastics) can be incorporated into the composites as disclosed in U.S. Patent Application Publication 2002/0198282 A1. Other organic-inorganic fillers such as zirconium methacrylate and zirconium dimethacrylate under the codes of CXZRO50 and CXZRO51 (Gelest, Inc.) can also be used. Suitable high refractive index filler materials such as high refractive index silica glass fillers; calcium silicate based fillers such as apatites, hydroxyapatites or modified hydroxyapatite compositions may also be used. Alternatively, inert, non-toxic radiopaque materials such as bismuth oxide ($Bi_2O_3$), bismuth oxychloride (BiOCl), zirconium oxide, barium sulfate, and bismuth subcarbonate in micro- or nanoscaled sizes may be used. In addition, fibrous fillers such as those disclosed in U.S. Pat. Nos. 6,013,694, 6,403,676 and 6,270,562 to Jia and Jia et al. may also be used.

Suitable fillers have particle sizes of about 0.01 to about 5.0 micrometers, and may further comprise bound or unbound silicate colloids of about 0.001 to about 0.2 micrometers. These additional fillers may also be treated with a silane-coupling agent to increase adhesion with the polymerizable (meth)acrylate. Commercially available silane treated fumed silica based on Aerosil A200 can be obtained from Degussa Corp under the names of Aerosil R711 and R7200.

The amount of total filler system in the self-etching and bonding dental resin cement composition can vary from about 30 to about 80 weight percent based on the total weight of the resin cement composition, specifically about 40 to about 70 weight, and more specifically about 50 to about 65 weight percent filler based on the total self-etching and bonding dental resin cement composition.

The amount of filler system in the first paste can be about 1 to about 80 weight percent based on the total weight of the cement composition, specifically about 20 to about 60 weight percent, and more specifically about 30 to about 50 weight percent based on the total weight of the cement composition. The amount of filler system in the second paste can be about 1 to about 80 weight percent based on the total weight of the cement composition, specifically about 20 to about 60 weight percent, and more specifically about 30 to about 50 weight percent based on the total weight of the cement composition.

Any of the present compositions may further include additional additives such as stabilizers (e.g. 3,5-di-tert-butyl-4-hydroxytoluene (BHT)), flavoring agents, disinfectants/medicates, color indicators, pH indicators, a fluoride source, tooth mineralization promoting agent and the like Suitable fluoride sources include, for example, sodium fluoride, stannous fluoride, sodium monofluorophosphate, calcium fluorophosphate, and the like. When present, fluoride-releasing compounds, excluding the glass ionomer filler, are used in quantities of up to about 2% by weight of the total self-etching and bonding dental resin cement composition.

In one embodiment, the self-etching and bonding dental resin cement composition generally is formulated by mixing a polymerizable (meth)acrylate carboxylic acid/anhydride, the copolymerizable multi-functional (meth)acrylates; the diluents; filler; and a curing system. The self-etching and bonding dental resin cement composition can then applied to the tooth to be repaired, and cured.

Alternatively, the self-etching and bonding dental resin cement composition is formulated as a two-paste system where the two pastes are combined prior to use. The first paste can contain a polymerizable (meth)acrylate carboxylic acid/anhydride, a copolymerizable multi-functional (meth)acrylate, a diluent, a filler, and a free radical polymerization initiator; and the second paste can contain a copolymerizable multi-functional (meth)acrylate, a diluent, a filler, optionally a polymerizable (meth)acrylate carboxylic acid/anhydride, and optionally a free radical polymerization initiator for visible/ultraviolet light polymerization. Each paste may further optionally comprise a stabilizer, a free-radical-type polymerization accelerator, and/or a UV absorber as long as the stability of the resulting individual paste is not compromised. The filler may include radiopaque materials and high refractive index fillers as described above.

When necessary, desired amounts of the two pastes are metered out and then mixed using a spatula or other appropriate blending equipment. The self-etching and bonding dental resin cement composition thus obtained is then placed in the tooth to be restored.

Use of the self-etching and bonding dental resin cement composition includes applying the self-etching and bonding dental resin cement composition to the tooth or the internal surface of a dental restoration being bonded, adhering the restoration onto the tooth surface, and allowing the cement composition to cure. The self-etching and bonding dental resin cement composition can be self-curable or light curable. The cure may be initiated through the use of actinic radiation, by raising the temperature of the mixture, or by simply waiting for the chemical self-cure. Specifically, the self-etching and bonding dental resin cement composition is actinic light curable, specifically visible light. A separate etching step or bonding step (e.g., application of a polymerizable dental adhesive system) need not be performed. The dental resin cement bonds to the tooth without the need for the tooth to be washed.

Useful dental restorative materials or cements that may be used together with the self-etching and bonding dental resin cement compositions include amalgam and non-amalgam dental restoratives. Examples of useful non-amalgam materials include composite resin restoratives, metal and metal alloy restoratives, ceramic/porcelain restorative, and the like. Suitable dental restoratives are those conventional in the art.

The self-etching and bonding dental resin cement composition when applied to a tooth enhances the adhesiveness of the tooth without the need for an etching or bonding step. The multi-step bonding protocols typical of current commercial resin cement systems generally tend to be a source of material waste and unreasonable technique sensitivity. The present self-etching and bonding dental resin cement composition not only reduce the number of steps normally involved in preparing a substrate surface and applying the dental restorative materials, but less waste and improved restorative or sealant results are obtained.

Furthermore, although conventional aggressive etchants are effective in cleaning the surface of dentin for improved wetting, they can also weaken the underlying sound dentin by excessive demineralization and disruption of collagen fibrils. These types of etchants typically require an aqueous rinse step to remove residual acid and soluble by-products. Also, the depth of demineralized, altered dentin resulting from the use of aggressive etchants may exceed the depth to which an adhesive resin can penetrate the dentin, resulting in a weakened, partially reinforced hybrid dentin zone, and thereby become vulnerable to failure. In contrast, the present compositions do not require the use of these etchants and are used as single step composition.

In one embodiment, the self-etching and bonding dental resin cement composition is substantially free of added water. As used herein "substantially free of added water" means that no water is purposely added to the cement compositions and excludes water present in the starting materials or absorbed from the surrounding environment.

Contemplated herein are prepackaged dual-syringe or dual-barrel cartridges containing the self-etching and bonding dental resin cement composition in the form of a two-paste system. Each paste is packaged containing a catalyst paste in one cartridge or syringe and a base paste in the other cartridge or syringe. The two pastes remain separated until use, each paste can be dispensed in the desired amounts, typically equal amounts, mixed together and applied. The prepackaged cartridges may further comprise printed instructions, guidelines or tips for mixing, dispensing, or measuring the components; and/or guidelines for use.

The following non-limiting examples illustrate the invention.

EXAMPLES

Materials used for the following examples include:

| Material | Description |
| --- | --- |
| 4-MET/4-META | 4-Methacryloyloxyethyltrimellitic anhydride from Polyscience, Inc. PA |
| BisGMA | 2,2'-Bis [4-(3-methacryloxy-2-hydroxy propoxy)-phenyl]-propane |
| UDMA | Urethane dimethacrylate |
| HEMA | 2-Hydroxyethyl methacrylate |
| TEGDMA | Tri(ethylene glycol) dimethacrylate |
| BPO | Benzoyl peroxide |
| DHEPT | Bis(hydroxyethyl)-p-toluidine |
| EDMAB | Ethyl 4-(dimethylamino)benzoate |
| Lucirin-TPO | Phosphine oxide photoinitiator from BASF Corp. |
| UV-5411 | Benzophenone UV absorber from American Cyanamid Company |
| BHT | 3,5-Di-tert-butyl-4-hydroxytoluene |
| BSA•Na | Benzenesulfinic acid sodium salt |
| CQ | DL-camphorquinone |
| BiOCl | Bismuth oxychloride |
| Ba-b-silicate glass filler | Silane treated barium-borosilicate glass filler |
| Glass ionomer filler | Surface active Ca—F—Al—Ba-silicate glass filler |
| Fumed silica | Amorphous/fumed silica filler |

Example 1

Self-etching and Bonding Dental Resin Cement Composition Containing 4-methacryloyloxyethyltrimellitic acid/anhydride In Example 1 a self-etching and bonding dental resin cement composition was prepared from 4-META, BisGMA, HEMA, UDMA, and TEGDMA according to the formula of Table 1. The example is a self-etching and bonding dental resin cement composition prepared from two-paste system, a catalyst paste and a base paste. For use as a dental cement, the working time and setting time of the composition is about three minutes and four and half minutes, respectively, when the base paste and catalyst paste are mixed in 1:1 ratio by volume and the material is not subject to a second curing process. In dual-cure mode, when the material, upon mixing the base paste and catalyst paste, is subject to a dental visible light-curing source, the mass of the material will harden immediately upon the photoinitiation.

TABLE 1

| Resin compositions used | Catalyst resin: |
| --- | --- |
| to form catalyst and base pastes | BPO 2.75 wt %, BHT 0.2 wt % in 4-META/BisGMA/HEMA (wt. Ratio: 60/10/30) |
| | Base resin: |
| | UV-5411 1.2 wt %, L-TPO 0.25 wt %, DHEPT 0.5 wt %, EDMAB 0.4 wt %, CQ 0.2 wt % in UDMA/TEGDMA (wt Ratio: 70/30) |
| Paste Components | Catalyst paste: |
| | Catalyst resin/Ba-b-silicate glass filler/BiOCl/fumed silica (wt Ratio: 45/56.5/1/0.5) |
| | Base paste: |
| | Base resin: 32 wt % Filler: 68 wt % total of T530, Ba-b-silicate glass filler, glass ionomer filler, and BSA•Na |

Examples 2-6

Self-etching and Bonding Dental Resin Cement Composition Containing 4-methacryloyloxyethyltrimellitic acid/anhydride In Examples 2-6 self-etching and bonding dental resin cement compositions were prepared from 4-MET/4-META, BisGMA, HEMA, UDMA, and TEGDMA. Base resin and catalyst resin formulations are provided in Table 2 (all components are in parts per hundred).

TABLE 2

| | Example 2a | | Example 3a | | Example 4a | | Example 5a | | Example 6a | |
|---|---|---|---|---|---|---|---|---|---|---|
| Component | Base | Catalyst | Base | Catalyst | Base | Catalyst | Base | Catalyst | Base | Catalyst |
| 4-MET/4-META | — | 60 | — | 60 | — | 60 | — | 50 | — | 50 |
| BisGMA | 70 | 10 | — | 10 | — | — | — | — | — | 10 |
| UDMA | — | — | 70 | — | 70 | 15 | 70 | 20 | 70 | — |
| HEMA | 30 | 30 | — | — | 30 | 25 | — | 30 | — | — |
| TEGDMA | — | — | 30 | 30 | — | — | 30 | — | 30 | 40 |
| EDMAB | 0.4 | — | 0.2 | — | 0.4 | — | 0.2 | — | 0.5 | — |
| BPO | — | 2.75 | — | 2.75 | — | 2.75 | — | 2.75 | — | 2.75 |
| DHEPT | 0.5 | — | 0.8 | — | 0.5 | — | 0.6 | — | 0.8 | — |
| Lucirin-TPO | 0.25 | — | 0.25 | — | 0.25 | — | 0.25 | — | 0.25 | — |
| UV-5411 | 1.2 | — | 1.2 | — | 1.2 | — | 1.2 | — | 1.2 | — |
| BHT | — | 0.2 | — | 0.2 | — | 0.2 | — | 0.2 | — | 0.2 |
| BSA•Na | 2.0 | — | 1.0 | — | 1.0 | — | 1.8 | — | 1.5 | — |
| CQ | 0.1 | — | — | — | 0.1 | — | — | — | 0.1 | — |

Self-etching and bonding dental resin cement compositions Examples 2-6 were prepared by compounding fillers according to Table 3 with the catalyst resins and base resins provided in Table 2 (all components are in parts per hundred).

TABLE 3

| | Example 2 | | Example 3 | | Example 4 | | Example 5 | | Example 6 | |
|---|---|---|---|---|---|---|---|---|---|---|
| Components | Base | Catalyst | Base | Catalyst | Base | Catalyst | Base | Catalyst | Base | Catalyst |
| Base resin mix | 32.6 | — | 32.6 | — | 32.6 | — | 32.6 | — | 32.6 | — |
| Catalyst resin mix | — | 45.0 | — | 45.0 | — | 45.0 | — | 45.0 | — | 45.0 |
| BiOCl | — | 46.5 | — | 46.5 | — | 46.5 | — | 46.5 | — | 46.5 |
| Fumed silica | 0.4 | 0.5 | 0.4 | 0.5 | 0.4 | 0.5 | 0.4 | 0.5 | 0.4 | 0.5 |
| Ba-b-silicate glass filler | 55.0 | — | 55.0 | — | 55.0 | — | 55.0 | — | 55.0 | — |
| Glass ionomer filler | 12.0 | — | 12.0 | — | 12.0 | — | 12.0 | — | 12.0 | — |

The base pastes and resin pastes of Examples 2-6 have similar viscosities and can be dispensed through a dual-barrel cartridge equally and mixed homogenously.

Examples 7-11

Shear Bonding Strength to Dentin

Table 4 contains the results of cementation/bonding tests of the self-etching and bonding dental resin cement compositions of Examples 2-6 between dentin and a ceramic (3G® ceramic material, Pentron Corp., Wallingford, Conn.). The bonding test method was as follows:

1. 3G® ceramic rods were fabricated with a dental porcelain furnace according to the ceramic firing temperature and conditions of the product. The 3G® ceramic rods used for the bonding test have final dimensions of about 3.2 mm diameter and 6-8 mm length, on which one end of the rod was sandblasted, cleaned and then silane treated as per the product instructions. The treated end will be contacting the bonding cement as in a tooth restoration. Each test group contains 5 samples.

2. Teeth samples were prepared to expose the dentin and then the teeth were mounted with an acrylic material leaving the dentin exposed, which were then subject to sand paper grinding under wet condition to have a same surface pattern for all the test groups.

3. The base paste and catalyst past of Example 2 cement material were mixed in equal amounts and applied onto the prepared, briefly dried tooth surface. The ceramic rod was then seated onto the cement surface under a 500 gram load with the aid of a BenCor Multi-test device (Danville Engineering, CA).

4. After the cement hardened, the bonded samples were transferred into a 100% humidity chamber held at 37° C. for 24 hours before the debond test.

5. The debond test was done in push shear mode using a BenCor testing device on an ATS testing machine. The load at which the bonded ceramic rod broke was recorded and the shear bonding strength of the testing sample was then calculated based on the rod surface area. Standard deviation is reported in parentheses.
6. The debond test was repeated using the cement materials of Examples 3-6.

TABLE 4

| | Examples | | | | |
|---|---|---|---|---|---|
| | Example 7 | Example 8 | Example 9 | Example 10 | Example 11 |
| Cement material | Base and catalyst paste of Example 2 | Base and catalyst paste of Example 3 | Base and catalyst paste of Example 4 | Base and catalyst paste of Example 5 | Base and catalyst paste of Example 6 |
| SBS, MPa (S.D.) | 21.9 (5.1) | 15.3 (0.9) | 20.3 (3.7) | 8.6 (1.9) | 9.8 (0.6) |

As a comparison, the cement formula containing unsaturated phosphoric acid resin disclosed in U.S. Pat. No. 6,730,715 to Jia was used as a bonding reference. The dentin bonding strength of the comparison material tested according to the method described above for examples 7-11 is in the range of 3-8 MPa, while the present cement compositions containing 4-MET/4-META have significantly greater bonding strengths.

Examples 12-14

Shear Bonding Strength to other Dental Materials

Shear bonding strength (SBS) of the compositions of Examples 3-5 to other substrates was also explored using the same procedure described above. The other dental restorative material substrates tested include Rexillium® III, a nickel chromium base alloy for dental bridge framework (Pentron); Sculpture™ Plus Crown and Bridge indirect composite material (Pentron Corp.); and $ZrO_2$ and $Al_2O_3$ dental ceramics.

TABLE 5

| | Examples | | |
|---|---|---|---|
| Cement material | Example 12 Base and catalyst paste of Example 3 | Example 13 Base and catalyst paste of Example 4 | Example 14 Base and catalyst paste of Example 5 |
| | SBS, MPa (S.D.) | | |
| Rx III | 19.3 (4.8) | 25.4 (6.3) | 13.2 (2.1) |
| Sculpture Plus | 12.2 (2.4) | 22.4 (3.1) | 18.5 (1.9) |
| $ZrO_2$ Ceramics | 14.7 (1.6) | 18.6 (2.6) | 17.2 (3.0) |
| $Al_2O_3$ Ceramics | 13.2 (2.1) | 12.5 (4.6) | 11.8 (1.7) |

The terms "a" and "an" do not denote a limitation of quantity, but rather denote the presence of at least one of the referenced item. The terms "first," "second," and the like, "primary," "secondary," and the like, as used herein do not denote any order, quantity, or importance, but rather are used to distinguish one element from another. "Optional" or "optionally" means that the subsequently described event or circumstance may or may not occur, and that the description includes instances where the event occurs and instances where it does not. The endpoints of all ranges directed to the same component or property are inclusive and independently combinable.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended embodiments.

What is claimed is:

1. A self-etching and bonding dental resin cement composition, comprising:
    a two-paste system that is combined prior to use,
    wherein a first paste comprises
        about 40 to about 80 weight percent of a first polymerizable (meth)acrylate carboxylic acid/anhydride based on the total weight of the first paste polymerizable material,
    wherein the first polymerizable (meth)acrylate carboxylic acid/anhydride is 4-(meth)acryloyloxymethyltrimellitic acid; 4-(meth)acryloyloxymethyltrimellitic anhydride; 4-(meth)acryloyloxyethyltrimellitic acid; 4-(meth)acryloyloxyethyltrimellitic anhydride; 4-(meth)acryloyloxypropylltrimellitic acid; 4-(meth)acryloyloxypropyltrimellitic anhydride; or a combination thereof;
        about 0.1 to about 30 weight percent of a first copolymerizable multi-functional (meth)acrylate, based on the total weight of the first paste polymerizable material;
        a first diluent;
        a first filler; and
        benzoyl peroxide free radical polymerization initiator;
    wherein a second paste comprises
        about 50 to about 95 weight percent of a second copolymerizable multi-functional (meth)acrylate, based on the total weight of the second paste polymerizable material;
        a second diluent;
        a second filler; and
        a plurality of free radical polymerization accelerators including at least two aromatic tertiary amines and at least one aromatic sulfinic acid salt, and
    wherein the self-etching and bonding dental resin cement composition is substantially free of added water.

2. The composition of claim 1, wherein the second polymerizable (meth)acrylate carboxylic acid/anhydride is independently selected from a compound according to structure (I):

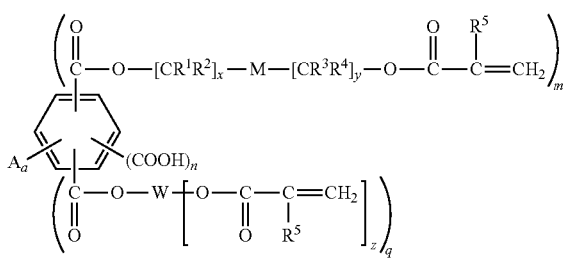

wherein
n is 0, 1, 2, 3, or 4;
q is 1, 2, 3, or 4;
A is an anhydride group;
a is 0 or 1;
$R^1$, $R^2$, $R^3$, and $R^4$ are each independently hydrogen, hydroxy, $C_1$-$C_{12}$ alkyl, $C_1$-$C_{12}$ perhaloalkyl, $C_1$-$C_{12}$ alkoxy, $C_1$-$C_{12}$ perhaloalkoxy, $C_2$-$C_{12}$ alkenyl, $C_2$-$C_{12}$ alkynyl, ($C_1$-$C_6$ alkyl)-O-($C_1$-$C_6$ alkylene), or hydroxy($C_1$-$C_6$ alkylene);
x and y are each independently an integer from 1 to 10;
$R^5$ is a hydrogen or methyl group;
M is a carbonyl-containing group, selected from

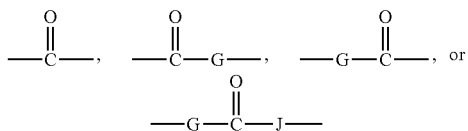

wherein G and J are each independently oxygen or $NR^6$, wherein $R^6$ is hydrogen or $C_1$-$C_6$ alkyl;
m is 0, 1, or 2; and
W is an aromatic or aliphatic hydrocarbyl linking group having a valency corresponding to z+1;
z is 1, 2, 3, 4, or 5; and
with the proviso that a and n are not both 0.

3. The composition of claim 1, wherein the second polymerizable (meth)acrylate carboxylic acid/anhydride is independently selected from a compound according to structure (II):

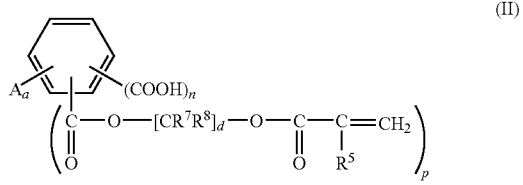

wherein
n is 0, 1, 2, 3, or 4;
A is an anhydride group;
a is 0 or 1;
p is 1, 2, 3, or 4;
$R^5$ is a hydrogen or methyl group;
$R^7$ and $R^8$ are each independently hydrogen, hydroxy, $C_1$-$C_{12}$ alkyl, $C_1$-$C_{12}$ perhaloalkyl, $C_1$-$C_{12}$ alkoxy, $C_1$-$C_{12}$ perhaloalkoxy, $C_2$-$C_{12}$ alkenyl, $C_2$-$C_{12}$ alkynyl, ($C_1$-$C_6$ alkyl)-O-($C_1$-$C_6$ alkylene), or hydroxy($C_1$-$C_6$ alkylene); and
d is 1 to 10; and
with the proviso that a and n are both not 0.

4. The composition of claim 1, wherein the first polymerizable (meth)acrylate carboxylic acid/anhydride is present in an amount of about 55 to about 65 weight percent based on the total weight of the first paste polymerizable material.

5. The composition of claim 1, wherein the first and second copolymerizable multi-functional (meth)acrylate is independently selected from a urethane (meth)acrylate, a urethane di(meth)acrylate; a polyurethane (meth)acrylate; a diurethane dimethacrylate; a polycarbonate di(meth)acrylate; an ethoxylated bisphenol A di(meth)acrylate; an ethoxylated trimethylolpropane tri(meth)acrylate; a diglycidyl (meth)acrylate adduct of Bisphenol A; or a combination thereof.

6. The composition of claim 1, wherein the first and second copolymerizable multi-functional (meth)acrylate is independently selected from a 2,2'-bis[4-(3-methacryloxy-2-hydroxy propoxy)-phenyl]-propane or a urethane di(meth)acrylate.

7. The composition of claim 1, wherein the first and second diluent is independently selected from a hydroxyalkyl (meth)acrylate; an ethylene glycol mono- or di-(meth)acrylate having one, two, three, or four repeat glycol units; a 1,2- or 1,3-propylene glycol mono- or di-(meth)acrylate having one, two, three, or four glycol repeat units; a $C_4$-$C_{12}$ diol di(meth)acrylate; a glycerol mono- or di-(meth)acrylate; a trimethylolpropane mono-, di-, or tri-(meth)acrylate; a pentaerythrifol mono-, di-, or tri-(meth)acrylate; a phenyl glycidyl ether (meth)acrylate; or a combination thereof.

8. The composition of claim 1, wherein the first and second diluent is independently selected from 2-hydroxyethyl acrylate; 2-hydroxyethyl methacrylate; 2-hydroxypropyl acrylate; 2-hydroxypropyl methacrylate; 4-hydroxybutyl acrylate; 4-hydroxybutyl methacrylate; ethylene glycol acrylate; ethylene glycol methacrylate; diethylene glycol acrylate; diethylene glycol methacrylate; tri(ethylene glycol)diacrylate; tri(ethylene glycol)dimethacrylate; tetra(ethylene glycol)diacrylate; tetra(ethylene glycol)dimethacrylate; 1,2- or 1,3-propylene glycol acrylate; 1,2- or 1,3-propylene glycol methacrylate; dipropylene glycol acrylate; dipropylene glycol methacrylate; tri(propylene glycol)diacrylate; tri(propylene glycol) dimethacrylate; tetra(propylene glycol)diacrylate; tetra(propylene glycol)dimethacrylate; 1,4-butanediol diacrylate; 1,4-butanediol dimethacrylate; 1,6-hexanediol diacrylate; 1,6-hexanediol dimethacrylate; or a combination thereof.

9. The composition of claim 1, wherein the first diluent is present in a total amount of about 1 to about 60 weight percent based on the total weight of the first paste polymerizable material; and
wherein the second diluent is present in a total amount of about 5 to about 50 weight percent based on the total weight of the second paste polymerizable material.

10. The composition of claim 1, wherein the first and the second filler is independently selected from silica, fumed silica, quartz, strontium silicate, strontium borosilicate, lithium silicate, lithium alumina silicate, amorphous silica, ammoniated or deammoniated calcium phosphate, tricalcium phosphate, alumina, zirconia, tin oxide, titania, barium-borosilicate glass filler, glass ionomer filler, an organic-inorganic filler, silica glass filler, calcium silicate, bismuth oxide, bismuth oxychloride, zirconium oxide, barium sulfate, bismuth subcarbonate, or a combination thereof.

11. The composition of claim 1, wherein the first paste further comprises a stabilizer; and
wherein the second paste further comprises an ultraviolet absorber, a polymerization accelerator, or a combination thereof.

12. A method of restoring a tooth, comprising:
mixing the first paste and the second paste of claim 1 to form a self-etching and bonding dental resin cement composition;

applying the self-etching and bonding dental resin cement composition to a tooth surface or a surface of a dental restoration being bonded without the use of any additional etching or bonding step prior to the applying;
applying the dental restorative material; and
curing the composition.

13. The method of claim 12, wherein the curing is by exposure to actinic radiation.

14. A method of making a dental restoration, comprising:
mixing the first paste and the second paste of claim 1 to form a self-etching and bonding dental resin cement composition;
applying the self-etching and bonding dental resin cement composition to a tooth surface or a surface of a dental restoration being bonded;
applying the dental restorative material; and
curing the composition.

15. A two-paste, dual-care self-etching and bonding dental resin cement composition, comprising a first and a second paste,
a.) wherein the first paste comprises
about 40 to about 80 weight percent of a polymerizable (meth)acrylate carboxylic acid/anhydride based on the total weight of the first paste polymerizable material, wherein the polymerizable (meth)acrylate carboxylic acid/anhydride is a 4-(meth)acryloyloxymethyltrimellitic acid; 4-(meth)acryloyloxymethyltrimellitic anhydride; 4-(meth)acryloyloxyethyltrimellitic acid; 4-(meth)acryloyloxyethyltrimellitic anhydride; 4-(meth)acryloyloxypropylltrimellitic acid; 4-(meth)acryloyloxypropyltrimellitic anhydride; or a combination thereof;
about 0.1 to about 30 weight percent of a first copolymerizable multi-functional (meth)acrylate selected from a urethane (meth)acrylate, a urethane di(meth)acrylate; a diurethane dimethacrylate; an ethoxylated bisphenol A di(meth)acrylate; an ethoxylated trimethylolpropane tri(meth)acrylate; a diglycidyl (meth)acrylate adduct of Bisphenol A; or a combination thereof, based on the total weight of the first paste polymerizable material;
a first diluent selected from a hydroxyalkyl (meth)acrylate; an ethylene glycol mono- or di-(meth)acrylate having one, two, three, or four repeat glycol units; a 1,2- or 1,3-propylene glycol mono- or di-(meth)acrylate having one, two, three, or four glycol repeat units; a $C_4$-$C_{12}$ diol di(meth)acrylate; a glycerol mono- or di-(meth)acrylate; a trimethylolpropane mono-, di-, or tri-(meth)acrylate; a pentaerythritol mono-, di-, or tri-(meth)acrylate; a phenyl glycidyl ether (meth)acrylate; or a combination thereof;
benzoyl peroxide free radical polymerization initiator; and
bismuth oxychloride, barium-borosilicate glass filler, fumed silica, or a combination thereof; and
b.) wherein the second paste comprises
about 50 to about 95 weight percent of a second copolymerizable multi-functional (meth)acrylate selected from a urethane (meth)acrylate, a urethane di(meth)acrylate; a diurethane dimethacrylate; an ethoxylated bisphenol A di(meth)acrylate; an ethoxylated trimethylolpropane tri(meth)acrylate; a diglycidyl (meth)acrylate adduct of Bisphenol A; or a combination thereof, based on the total weight of the second paste polymerizable material;
a second diluent selected from a hydroxyalkyl (meth)acrylate; an ethylene glycol mono- or di-(meth)acrylate having one, two, three, or four repeat glycol units; a 1,2- or 1,3-propylene glycol mono- or di-(meth)acrylate having one, two, three, or four glycol repeat units; a $C_4$-$C_{12}$ diol di(meth)acrylate; a glycerol mono- or di-(meth)acrylate; a trimethylolpropane mono-, di-, or tri-(meth)acrylate; a pentaerythritol mono-, di-, or tri-(meth)acrylate; a phenyl glycidyl ether (meth)acrylate; or a combination thereof;
a plurality of free radical polymerization accelerators including at least two aromatic tertiary amines and at least one aromatic sulfinic acid salt;
a photoinitiator; and
barium-borosilicate glass filler, silane treated barium-borosilicate glass filler, glass ionomer filler, fumed silica, or a combination thereof, and
wherein the self-etching and bonding dental resin cement composition is substantially free of added water.

16. The two-paste, dual-care self-etching and bonding dental resin cement composition of claim 15,
a.) wherein the first paste comprises
a polymerizable (meth)acrylate carboxylic acid/anhydride selected from 4-methacryloyloxyethyltrimellitic acid, 4-methacryloyloxyethyltrimellitic acid anhydride, or a combination thereof;
a first copolymerizable multi-functional (meth)acrylate selected from a urethane dimethacrylate, 2,2'-bis[4-(3-methacryloxy-2-hydroxy propoxy)-phenyl]-propane or a combination thereof;
a first diluent selected from 2-hydroxyethyl methacrylate, triethyleneglycol dimethacrylate, or a combination thereof;
benzoyl peroxide free radical polymerization initiator; and
bismuth oxychloride, barium-borosilicate glass filler, fumed silica, or a combination therefore; and
b.) wherein the second paste comprises
a second copolvmerizable multi-functional (meth)acrylate selected from a urethane dimethacrylate, 2,2'-bis[4-(3-methacryloxy-2-hydroxy propoxy)-phenyl]-propane or a combination thereof; and
a second diluent selected from 2-hydroxyethyl methacrylate, triethyleneglycol dimethacrylate, or a combination thereof;
a plurality of free radical polymerization accelerators including ethyl 4-(dimethylamino)benzoate (EDMAD), bis(hydroxyethyl)-p-toluidine (DHEPT), and benzenesulfinic acid sodium salt (BSA.Na);
a photoinitiator; and
barium-borosilicate glass filler, silane treated barium-borosilicate glass filler, glass ionomer filler, fumed silica, or a combination thereof.

17. The two-paste, dual-cure self-etching and bonding dental resin cement composition of claim 15, wherein the plurality of free radical polymerization accelerators includes ethyl 4-(dimethylamino)benzoate (EDMAB), bis(hydroxyethyl)-p-toluidine (DHEPT), and benzenesulfinic acid sodium salt (BSA.Na).

18. The composition of claim 1, wherein the plurality of free radical polymerization accelerators includes ethyl 4-(dimethylamino)benzoate (EDMAB), bis(hydroxyethyl)-p-toluidine (DHEPT), and benzenesulfinic acid sodium salt (BSA.Na).

19. The composition of claim 18, wherein the two-paste system is a dual-cure system wherein the second paste further comprises a photoinitiator.

* * * * *

UNITED STATES PATENT AND TRADEMARK OFFICE
CERTIFICATE OF CORRECTION

PATENT NO. : 7,906,564 B2
APPLICATION NO. : 11/360314
DATED : March 15, 2011
INVENTOR(S) : Jia et al.

Page 1 of 1

It is certified that error appears in the above-identified patent and that said Letters Patent is hereby corrected as shown below:

Col. 3, line 13, "x and y is" should read --x and y are--.

Col. 3, line 14, "$R^1$, $R^2$, $R^3$, and $R^4$ is" should read --$R^1$, $R^2$, $R^3$, and $R^4$ are--.

Col. 3, line 51, "x and y is" should read --x and y are--.

Col. 4, line 23, "R8" should read --$R^8$--.

Col. 6, line 52, "LUCIIN™" should read --LUCIRIN™--.

Col. 8, line 24, "and the like Suitable" should read --and the like. Suitable--.

Col. 8, line 36, "can then applied" should read --can then be applied--.

Col. 9, line 22, "only reduce" should read --only reduces--.

Col. 13, line 58, "referenced item" should read --referenced items--.

Col. 15, line 67, Claim 3, "are both not 0." should read --are not both 0.--.

Col. 16, line 6, Claim 5, "(meth)acrylate is" should read --(meth)acrylates are--.

Col. 16, line 14, Claim 6, "(meth)acrylate is" should read --(meth)acrylates are--.

Col. 16, line 18, Claim 7, "diluent is" should read --diluents are--.

Col. 16, line 24, Claim 7, "pentaerythrifol" should read --pentaerythritol--.

Col. 16, line 28, Claim 8, "diluent is" should read --diluents are--.

Col. 16, line 51, Claim 10, "second filler is" should read --second fillers are--.

Col. 16, line 60, Claim 10, "subearbonate" should read --subcarbonate--.

Col. 16, lines 62-63, Claim 11, "absorber, a polymerization accelerator, or a combination thereof." should read --absorber.--.

Col. 18, line 34, Claim 16, "or a combination therefore; and" should read --or a combination thereof; and--.

Col. 18, line 36, Claim 16, "copolvmerizable" should read --copolymerizable--.

Col. 18, lines 44-45, Claim 16, "(ED-MAD)" should read --(ED-MAB)--.

Signed and Sealed this
Fourteenth Day of June, 2011

David J. Kappos
*Director of the United States Patent and Trademark Office*